(12) United States Patent
Tolentino et al.

(10) Patent No.: US 6,534,614 B2
(45) Date of Patent: Mar. 18, 2003

(54) PROCESS FOR THE PRODUCTION OF LINEAR ORGANOHYDROGENSILOXANES

(75) Inventors: Luisito A. Tolentino, Clifton Park, NY (US); Akber Ali Khanshab, Schenectady, NY (US)

(73) Assignee: General Electric Company, Pittsfield, MA (US)

( * ) Notice: Subject to any disclaimer, the term of this patent is extended or adjusted under 35 U.S.C. 154(b) by 0 days.

(21) Appl. No.: 09/825,795

(22) Filed: Apr. 4, 2001

(65) Prior Publication Data

US 2002/0173613 A1 Nov. 21, 2002

(51) Int. Cl.$^7$ ................................................. C08G 77/10
(52) U.S. Cl. ........................... 528/12; 526/68; 556/451; 556/469; 556/470; 528/12; 528/31; 528/33; 528/37; 528/23
(58) Field of Search ............................ 526/68; 556/451, 556/469, 470; 528/12, 31, 33, 37, 23

(56) References Cited

U.S. PATENT DOCUMENTS

| | | | |
|---|---|---|---|
| 2,491,843 A | * | 12/1949 | Wilcock |
| 5,396,956 A | | 3/1995 | Cherewyk et al. |
| 5,670,596 A | | 9/1997 | Razzano et al. |
| 5,698,654 A | | 12/1997 | Nye et al. |
| 5,753,751 A | | 5/1998 | Liao et al. |
| 6,143,912 A | * | 11/2000 | Lindner et al. |

* cited by examiner

*Primary Examiner*—Margaret G. Moore
*Assistant Examiner*—Kuo-Liang Peng
(74) *Attorney, Agent, or Firm*—Kenneth S. Wheelock

(57) ABSTRACT

A process for preparing linear organohydrogensiloxanes. The process comprises contacting an organohydrogendichlorosilane in the presence of trimethylchlorosilane with water to form an M-stopped hydrolyzate. The hydrolyzate is optionally preheated prior to being contacted with an acidic rearrangement catalyst to effect formation of linear organohydrogensiloxanes. The linear organohydrogensiloxanes are separated from cyclic organohydrogensiloxanes and recovered. The cyclic organohydrogensiloxanes may then be recycled to the process for further contact with the acidic rearrangement catalyst for maximum overall conversion rate.

13 Claims, No Drawings

PROCESS FOR THE PRODUCTION OF LINEAR ORGANOHYDROGENSILOXANES

FIELD OF THE INVENTION

The present invention relates to a process for the production of linear organohydrogenpolysiloxanes.

BACKGROUND OF THE INVENTION

Linear organohydrogenpolysiloxanes are used in coatings, textiles and paper release applications. They are also used as source of SiH for catalyzed silicone addition cure with vinyl functional silicones.

Organohydrogenpolysiloxanes are typically prepared by hydrolysis of organohydogenpolysiloxane ($RSiHCl_2$) with or without a chainstopper such as trimethylchlorosilane. The product is a mixture of linear and cyclic silicone hydride with the latter as the minor component. U.S. Pat. No. 5,395,956 discloses a continuous process of preparing cyclic organohydrogensiloxanes by contacting an organohydrogendichlorosilane with about a stoichiometric equivalent of water to form a hydrolyzate, an equilibrium mixture containing cyclic and linear organohydrogensiloxanes. The hydrolyzate is then rearranged by contact with an acidic rearrangement catalyst to effect formation of cyclic organohydrogensiloxanes. In U.S. Pat. No. 5,698,654, the ring opening polymerization of cyclic organosiloxanes is done in the presence of a basic catalyst and by the neutralization of the basic catalyst with an excess of a catalytic Lewis acid compound.

Since the majority of applications require materials containing mostly linear species, it is common in the art to flash strip or distill the hydrolyzate to remove the cyclic species. As the demand for linear organohydrogenpolysiloxanes grows, the amount of cyclic species also grows. There is still a need for an improved method for recycling the cyclic species and converting them to linear species.

SUMMARY OF THE INVENTION

The present invention relates to a process for preparing linear organopolysiloxanes, which comprises contacting organodichlorosilane in the presence of trimethylchlorosilane with water to form M-stopped hydrolyzate.

The hydrolyzate is contacted with an acidic rearrangement catalyst at a temperature of about 65° C. or lower to effect the formation of linear organopolysiloxanes. The linear organopolysiloxanes are separated from the cyclic organopolysiloxanes and recovered.

DESCRIPTION OF THE INVENTION

The present invention is a process for preparing linear organohydrogensiloxanes by converting volatile cyclic organohydrogensiloxanes in hydride hydrolyzates into linear organohydrogensiloxanes.

Preparing hydride hydrolyzate feed. The feed to the process of the present invention, hydride hydrolyzates or organomethyl-hydrosiloxanes are well-known in the silicone art and may be prepared by any suitable technique. In this step, halosilanes exemplified by the formula of $RHSiCl_2$ (1) are placed in contact with water in the presence of a chain stopper to form a hydrolyzate comprising cyclic organohydrogensiloxanes and linear organohydrogensiloxanes.

The silanes may be a single species of silane or may be a mixture of such silanes. The substituent R in formula (1) R is selected from a group consisting of saturated monovalent hydrocarbon radicals comprising one to 12 carbon atoms and aryl radicals. R can be, for example, methyl, ethyl, propyl, isopropyl, butyl, tertiary butyl, sec-butyl, hexyl, cyclohexyl, dodecyl, phenyl, tolyl, and naphthyl. In one embodiment, R is selected from a group consisting of methyl and phenyl. In another embodiment, R is methyl and methyldichlorosilane is used. In yet another embodiment, trimethylchlorosilane $(CH_3)_3SiCl$ is added in less than 5 wt. % as a chain stopper to stop polymerization and control the viscosity of the finished fluid.

The ratio of cyclic to linear in the M-stopped hydrolyzate in the present invention, as well as the chain length of the linear siloxane, varies depending on the conditions of the hydrolysis, such as the ratio of halosilane to water, temperature, contact, time, and solvents. M-stopped hereby, as commonly known in the art, refers to the tri-functional organosilane end groups $R_{1,2,3}SiO_{1/2}$ at the end of the chain, wherein each of the $R_1$, $R_2$, and $R_3$ is independently selected from one to forty carbon atom monovalent hydrocarbon radicals. In one embodiment, M is trimethylsilyl.

In one embodiment of this hydrolysis reaction, the silane is contacted with excess water, where a stoichiometric equivalent of water is defined as 0.5 mole of water per mole of halogen provided to the process by the silane. In another embodiment, the mole ratio of water to silane is 100 to 200% of stoichiometric equivalence.

Contact of the silane with the water can be conducted in standard reactors for hydrolyzing halosilanes. In one embodiment, the process is at a pressure at which the silane is present as a liquid phase. The hydrolysis process can be conducted at a temperature at about −15° C. to about 50° C. In one embodiment, the hydrolysis process is conducted at a temperature within a range of about 5° C. to 30° C.

The M-stopped hydrolyzate feed to the process of the present invention typically has a weight ratio of about 0.5:1 to 4:1 of cyclic organohydrogensiloxanes to linear organohydrogensiloxanes.

In one embodiment, the hydrolyzate formed in the hydrolysis process prior to being fed to the rearrangement process of the present invention is flash distilled to separate the cyclic organohydrogensiloxanes from the linear organohydrogensiloxanes. The flash distillation is typically a known standard method for separating cyclic siloxanes from mixtures for a feed stream with primarily cyclic. In one embodiment, the hydrolyzate is stripped at about 150° C. at 5 mm Hg to give an overhead stream comprising primarily trace hexamethyl disiloxane, mixed cyclics $D_4$–$D_5$ and low-boiling linear species. The overhead stream is then fed to the rearrangement process to convert the cyclic species into linears.

In one embodiment of the invention, the M-stopped hydrolyzate feed to the rearrangement process of the present invention is in the form of being diluted in an inert solvent. By the term "inert" it is meant a solvent which can serves as a diluent and does not otherwise react in the process. In one embodiment, the inert solvents are those alkanes and mixtures of alkanes having a boiling point above that of the cyclic heptamer of the organohydrogensiloxane Optional preheating step. In one embodiment, the M-stopped hydrolyzate feed is preheated to a temperature of about 35° C. to 55° C. in a heat exchanger prior to the rearrangement step comprising passing the hydrolyzate through an acid rearrangement catalyst. The preheating is optional to cut down on the residence time in the acid rearrangement reactor.

Rearranging the hydrolyzate feed. In this process, the M-stopped hydrolyzate feed, after the optional pre-heating step if desired, is passed through an acid rearrangement catalyst. Acid rearrangement catalysts can be any acid which facilitates rearrangement of cyclic organohydrogensiloxanes to linear organohydrogensiloxanes. The acidic rearrangement catalyst can be an Arhennius, Bronsted, or a Lewis acid. The acidic rearrangement catalyst can be a homogeneous catalyst such as hydrogen chloride, sulfuric acid, or chlorosulfonic acid. It can be a heterogeneous acid such as bentonite clays such as Super Filtrol F-I O (Engelhard Corporation, Jackson, Miss.). In one embodiment, the acidic rearrangement catalyst is a porous solid such as carbon, a clay, or a zeolite having absorbed thereto an acid such as sulfuric or phosphoric acid. Alternatives to acidic polymerization medium including art-known strong acid cationic ion exchange resins can be used, an example of which is Nafion® (Aldrich Chemical Company, Milwaukee, Wis.), a sulfonic acid functionalized fluoropolymer. Others include standard sulfonic acid functionalized styrene-divinylbenzene (H) ion exchange resins.

The temperature at which the rearrangement can be run is about 65° C. or lower. In one embodiment, the temperature is within a range of about 18° C. to 65° C. In another embodiment, the temperature is within a range of about 40° C. to 55° C.

In one embodiment of the invention, the pressure of the rearrangement process is at or about ambient pressure.

The rearrangement process of the present invention is carried out in a fixed-bed or stirred-bed. It can be run as a continuous, semi-continuous, or batch process. In one embodiment, the process is run as a continuous process using a fixed-bed of the acidic rearrangement catalyst.

The residence time in the rearrangement reactor is about two hours or less. In one embodiment, the residence time is within a range of about five to an hour. In another embodiment, the residence time for a continuous process is about five to thirty minutes.

The conversion rate of cyclic to linear in rearrangement step as well as the chain length of the linear siloxane varies depending on the feed composition, the residence time in the preheater as well as the conditions of the rearrangement reaction.

Recovering linear organohydrogensiloxanes. The linear organohydrogensiloxanes (from rearrangement of cyclic organohydrogensiloxanes) are described by formula: $MD_nM$, wherein:

M: as previously described, refers to the tri-functional organosilane end groups $R_{1,2,3}SiO_{1/2}$ at the end of the chain D.

D: $R_4HSiO_{2/2}$ and wherein n is an integer of 1 or higher, and each of $R_1$, $R_2$, $R_3$, and $R_4$ is independently selected from one to forty carbon atom monovalent hydrocarbon radicals. In one embodiment, the linear organohydrogensiloxanes recovered from the present process are those where R is methyl and n is 1 or higher, and mostly in the range of 20 to 80.

The method for recovering the linear organohydrogensiloxanes from the present process is not critical and can be standard methods known in the art for separating linear and cyclic siloxanes mixtures. For example, the rearranged hydrolyzate can be flash distilled to separate the volatile cyclic organohydrogensiloxanes and recover the linear organohydrogensiloxanes.

In one embodiment, the volatile cyclic siloxanes are recycled and sent back to the rearrangement reactor as a separate feed stream by themselves for further rearrangement or optionally mixed with the incoming M-stopped hydrolyzate feed. Continuous runs of the rearrangement process of the present invention with continuous recycled of the recovered cyclics provide a theoretical yield of greater than 99 percent of the chlorosilane feed being converted to linear organohydrogen siloxanes.

EXAMPLES

The following examples are provided to illustrate the present invention. They are not intended to limit the present claims.

Comparative Example 1

A mixture of 96.5 wt. % methyldichlorosilane and 3.5 wt. % trimethylchlorosilane was mixed with 200% excess of stoichiometric equivalent of water in a hydrolysis reactor i.e. 0.5 mole of water per mole of silicon bonded chlorine added to the reactor. The hydrolysis reactor was maintained at 60 psig and the temperature of the reactor was controlled such that the hydrolyzate exiting the reactor was at a temperature of about 33° C. The organohydrogen siloxane hydrolyzate exiting the reactor was analyzed by gas chromatography (GC) using a thermal conductivity detector (TCD) and found to comprise about 80 weight percent M-stopped linear organohydrogensiloxane species and about 20 weight percent cyclic organohydrogensiloxane species. The viscosity of the hydrolyzate is about 10–20 centistokes and a % weight loss (at 150° C./ hour) of about 15–20%.

The hydrolyzate from the hydrolysis reactor was vacuum flash distilled at about 150° C. at 5 mm Hg and the cyclic species and low-boiling linear species taken overhead. The bottom linear fraction was cooled and recovered. The overhead fraction was analyzed by gas chromatography (GC) and found to contain about 20 wt. % linears and 80 wt. % mixed cyclics of primarily $D_4$–$D_5$, with the rest of the cyclics being primarily $D_6$–$D_7$. The overhead stream with 79.8% "volatiles," a mixture of primarily cyclics and some linears was used as the feed stream for examples 2–10.

Examples 2–10

The M-stopped hydrolyzate feed from example 1 was pumped at the rate of 1.3 to 5.4 g/min. through a preheater maintained at about 35 to 55° C., followed by a single pass through a packed bed reactor containing about 100 grams of Filtrol 25 bentonite acid leached granules catalyst at a bed temperature of either 35, 45, or 55° C. The residence time of the rearrangement reactor was controlled by the pump rate. The product exiting the reactor was analyzed by gas chromatography (GC) using a thermal conductivity detector (TCD) for volatile content (i.e., indicator of cyclic presence), viscosity, and % weight loss (at 150° C./ hour).

Examples 11–17

In these examples, the product exiting the reactor was stripped at about 150° C. at 5 mm Hg to reduce the volatiles (cyclics) content to less than or about 3 wt. %. The material recovered from the receiver was re-used as feed to the rearrangement reactor by blending with the hydrolyzate feed of example 1 at a ratio of 15 wt. % volatile and 85 wt. % original hydrolyzate feed. For example 11 (comparative), the feed stream bypassed the rearrangement reactor and was analyzed for volatile content, viscosity, and % weight loss (at 150° C./ hour). The percent of "volatiles," a mixture of primarily cyclics and some linears was found to be at 39.26 wt. %.

For examples 12–17, the "mixed" hydrolyzate feed was pumped at the rate of 1.3 to 5.4 g/min. through a preheater maintained at about 35 to 55° C., followed by a single pass through a packed bed reactor containing about 100 grams of Filtrol 25 bentonite acid leached granules catalyst at a bed temperature of either 35, 45, or 55° C. with the residence time being controlled by the pump rate. The product was analyzed for volatile content, viscosity, and % weight loss (at 150° C./hour). The results of examples are as follows:

TABLE I

| Examples | Feed Material | Temp. ° C. | Residence Time (min) | Viscosity @ 25° C. cstks | % weight loss | % volatiles |
|---|---|---|---|---|---|---|
| Comparative 1 | Volatile hydride | 25 | 0 | 2 | 65 | 79.8 |
| 2 | Volatile hydride | 35 | 8 | 11.5 | 15.06 | 26.63 |
| 3 | Volatile hydride | 35 | 18 | 16.4 | 9.25 | 14.98 |
| 4 | Volatile hydride | 35 | 35 | 16.3 | 8.62 | 13.16 |
| 5 | Volatile hydride | 45 | 8 | 14 | 10.01 | 16.1 |
| 6 | Volatile hydride | 45 | 18 | 15.7 | 8.99 | 14.16 |
| 7 | Volatile hydride | 55 | 35 | 17 | 8.75 | 13.27 |
| 8 | Volatile hydride | 55 | 8 | 15.6 | 9.22 | 13.93 |
| 9 | Volatile hydride | 55 | 18 | 16.7 | 8.8 | 14.00 |
| 10 | Volatile hydride | 55 | 38 | 19.6 | 8.24 | 13.03 |
| Comparative 11 | Hydride mix. | 25 | 0 | 12 | 28.88 | 39.25 |
| 12 | Hydride mix. | 35 | 9 | 14.2 | 8.68 | 21.82 |
| 13 | Hydride mix. | 35 | 17 | 14.75 | 8.58 | 15.86 |
| 14 | Hydride mix. | 35 | 30 | 14.45 | 8.47 | 16.16 |
| 15 | Hydride mix. | 55 | 9 | 15.65 | 8.56 | 16.09 |
| 16 | Hydride mix. | 55 | 17 | 15.4 | 8.56 | 13.90 |
| 17 | Hydride mix. | 55 | 30 | 16.5 | 8.57 | 13.97 |

We claim:

1. A process for preparing linear organohydrogensiloxanes, the process comprising:
   (A) contacting a silane of the formula $RHSiCl_2$ with water in the presence of trimethylchlorosilane to form a hydrolyzate comprising cyclic organohydrogensiloxanes and linear organohydrogensiloxanes,
   (B) contacting the hydrolyzate with an acidic rearrangement catalyst at a temperature of about 65° C. or less thereby increasing the ratio of the linear organohydrogensiloxanes to the cyclic organohydrogensiloxanes, and
   (C) separating the linear organohydrogensiloxanes from the cyclic organohydrogensiloxanes;

where R is selected from the group consisting of saturated monovalent hydrocarbon radicals comprising one to 12 carbon atoms and aryl radicals.

2. A process according to claim 1, further including preheating the hydrolyzate at a temperature of about 35° C. to 55° C. prior to contacting said hydrolyzate with an acidic rearrangement catalyst.

3. A process according to claim 1, wherein the mole ratio of water to silane is about 100 to 200% of stoichiometric equivalence.

4. A process according to claim 1, wherein the hydrolyzate is in contact with the acidic rearrangement catalyst for about at least five minutes.

5. A process according to claim 1, wherein the hydrolyzate is in contact with the acidic rearrangement catalyst at atmospheric pressure.

6. A process according to claim 1, wherein the hydrolyzate used in (B) is a distillate of product from a process comprising the reaction of a silane of the formula $RHSiCl_2$ with water in the presence of trimethylchlorosilane.

7. A process according to claim 1, wherein said hydrolyzate is in contact with the acidic rearrangement catalyst in a fixed bed reactor.

8. A process according to claim 1, wherein the process is run as a continuous process.

9. A process according to claim 8, wherein the cyclic organohydrogensiloxanes are recovered and recycled to the continuous process.

10. A process according to claim 1, wherein the acidic rearrangement catalyst is a heterogeneous catalyst.

11. A process according to claim 10, where the acidic rearrangement catalyst is selected from the group consisting of carbon, clay, and zeolite having absorbed thereto a protic acid.

12. A process according to claim 11, where the acid is selected from the group consisting of sulfuric acid and phosphoric acid.

13. A process according to claim 10, where the acidic rearrangement catalyst is a sulfonated divinylbenzenestyrene copolymer resin.

* * * * *